United States Patent
Huet

(10) Patent No.: US 6,595,981 B2
(45) Date of Patent: Jul. 22, 2003

(54) AUTOMATICALLY-CLOSING CONNECTOR FOR CONNECTING A LIQUID INJECTION HEAD TO AN INJECTION OUTLET

(75) Inventor: Jean-Max Huet, Clichy (FR)

(73) Assignee: Vygon, Ecouen (FR)

( * ) Notice: Subject to any disclaimer, the term of this patent is extended or adjusted under 35 U.S.C. 154(b) by 0 days.

(21) Appl. No.: 09/738,342

(22) Filed: Dec. 15, 2000

(65) Prior Publication Data

US 2001/0004686 A1 Jun. 21, 2001

(30) Foreign Application Priority Data

Dec. 16, 1999 (FR) .......................................... 99 15898

(51) Int. Cl.$^7$ ............................................ A61M 25/00
(52) U.S. Cl. ...................................................... 604/523
(58) Field of Search ................................. 604/523, 246, 604/247, 249, 533–535, 537, 538, 539, 284, 93.01, 264

(56) References Cited

U.S. PATENT DOCUMENTS 5,776,113 A * 7/1998 Daugherty et al. ......... 604/280

FOREIGN PATENT DOCUMENTS

| FR | 2 604 237 A | 3/1988 |
| WO | 98 17192 A | 4/1998 |

* cited by examiner

*Primary Examiner*—Brian L. Casler
*Assistant Examiner*—Ann Y Lam
(74) *Attorney, Agent, or Firm*—Levine & Mandelbaum

(57) ABSTRACT

The invention relates to an automatically-closing connector. The connector has a closing piston which is rigid and non-deformable; a compression chamber is constituted around the closing piston and is defined upstream by the end wall of the housing and downstream by a peripheral sealing gasket carried by the piston; the outlet of the connector is situated downstream from this gasket and the closing piston has an internal passage with an inlet that opens out into the compression chamber and an outlet that communicates with the outlet of the connector. The connector is applicable to injection devices in the medical field.

14 Claims, 3 Drawing Sheets

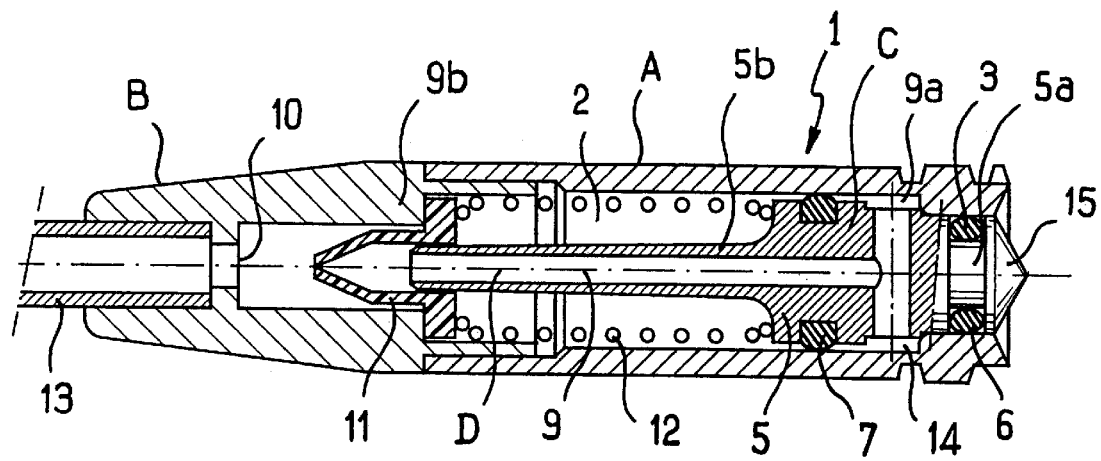
FIG_1
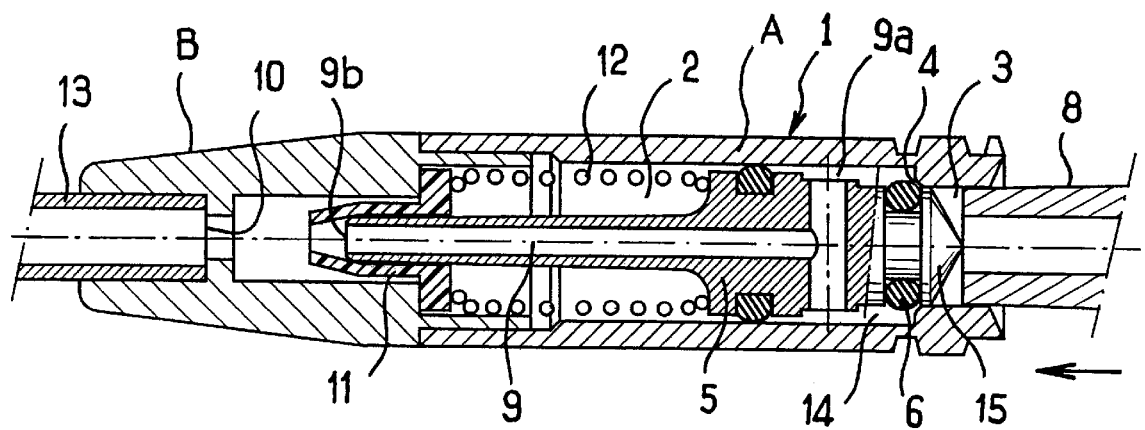
FIG_2
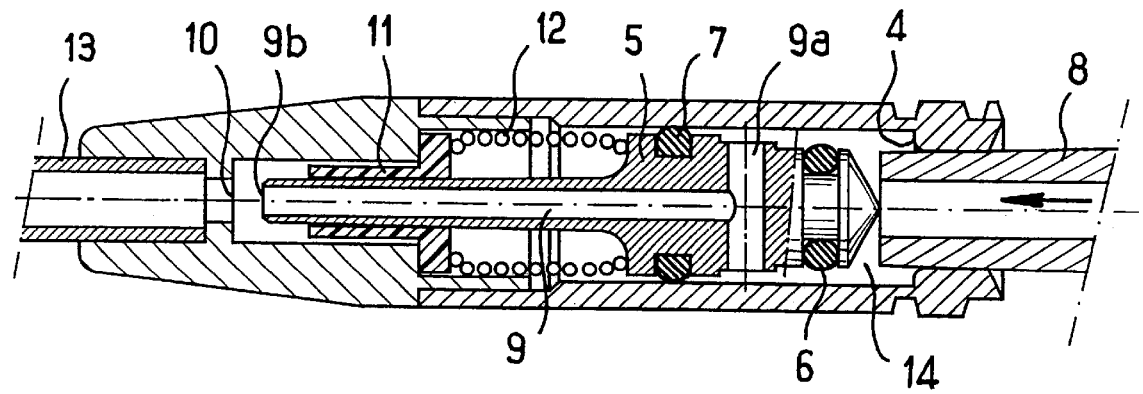
FIG_3

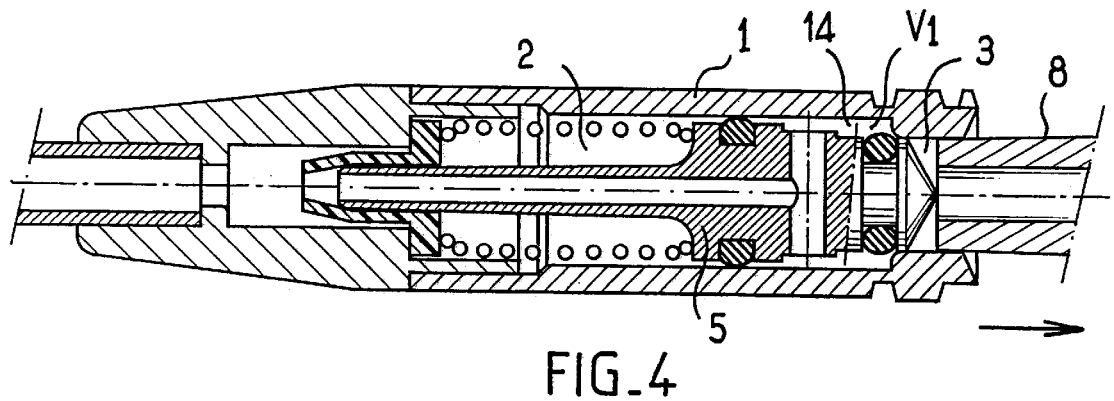
FIG_4
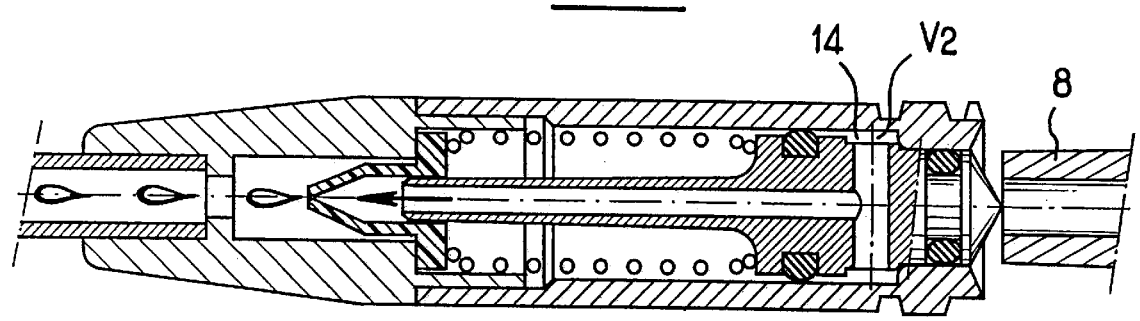
FIG_5
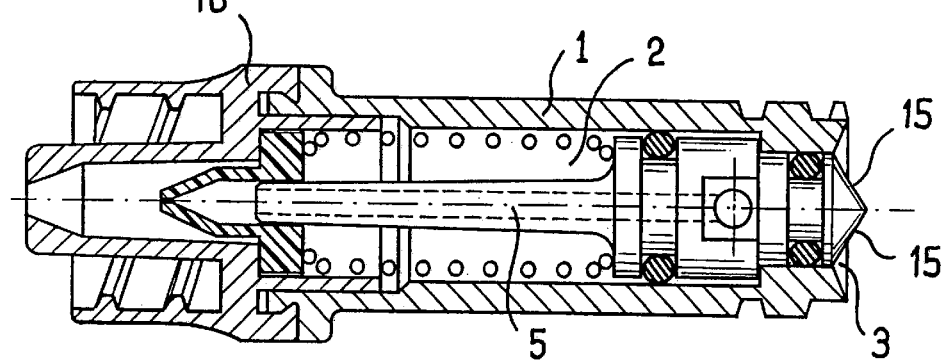
FIG_6
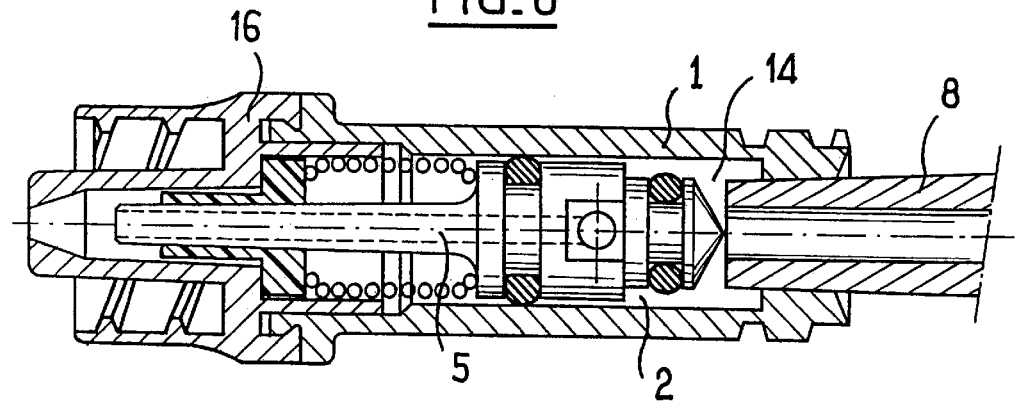
FIG_7

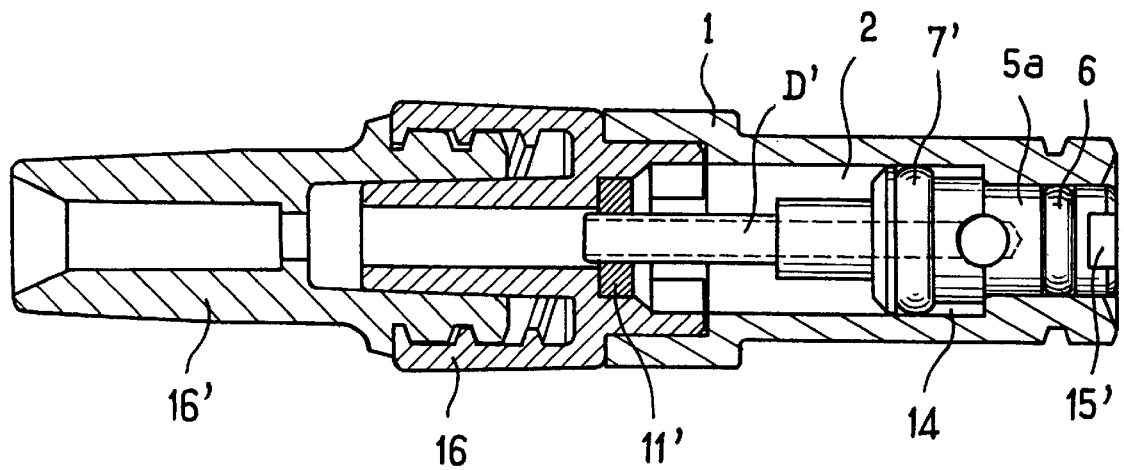
FIG_8
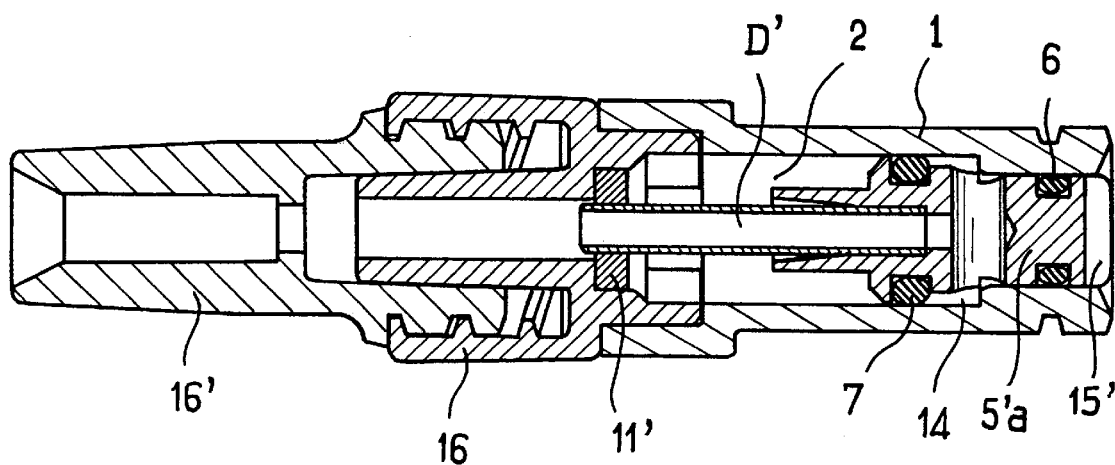
FIG_9

AUTOMATICALLY-CLOSING CONNECTOR FOR CONNECTING A LIQUID INJECTION HEAD TO AN INJECTION OUTLET

The invention relates to an automatically-closing connector for connecting a liquid injection head to an injection outlet.

BACKGROUND OF THE INVENTION

The connector is suitable in particular for medical use and more particularly for connecting an injection head and a catheter tube or other duct of a liquid pathway to enable liquid to be inserted into the body.

Automatically-closing connectors are known that comprise a case which defines a housing which is accessible via an injection inlet duct opening out into the housing through an end wall of the housing, said chamber communicating with an injection outlet, and the inlet duct being designed to enable the injection head to be inserted with lateral sealing into said duct towards the housing, and the connector including a closing piston which is movable in the housing and in the inlet duct between an upstream position in which it closes the duct and towards which it is urged by resilient return means, and a downstream position in which it no longer closes the duct and towards which it is pushed by the injection head when the injection head is inserted into the inlet passage.

An example of such a connector is described in European patent EP 0 544 581 and the corresponding U.S. Pat. No. 5,380,306.

Withdrawing the injection head after an injection operation can cause the patient's blood to flow back into the liquid pathway which connects the connector to the patient, thus running the risk of said pathway subsequently being blocked by coagulated blood.

To avoid this back flow, it is known to provide the connector with a compression chamber that is accessible to the liquid injected by the injection head and which communicates with the outlet of the connector, said chamber being designed so that its volume varies under the effect of the displacement of the closing piston so that withdrawing the injection head causes the volume of the chamber to be reduced and excess liquid to be expelled from the chamber towards the outlet, thereby establishing pressure that opposes the back flow of blood in the pathway leading to the patient.

Publication WO 98/17192 describes an example of a connector implementing that concept.

In that example, the compression chamber is constituted inside the closing piston which is complex in structure.

OBJECTS AND SUMMARY OF THE INVENTION

An object of the invention is to provide a connector which has a compression chamber while remaining simple in structure.

According to the invention, this is achieved by a connector which comprises a case which defines a housing which is accessible via an injection inlet duct opening out into the housing through an end wall (4) of the housing, said housing communicating with an injection outlet of the connector, and the inlet duct being designed to enable the injection head to be inserted with lateral sealing into said duct towards the housing, the connector including a rigid and non-deformable closing piston which is movable in the housing and in the inlet duct between an upstream position in which it closes the duct and towards which it is urged by resilient return means, and a downstream position in which it no longer closes the duct and towards which it is pushed by the injection head when the head is inserted into the inlet passage, the connector having a compression chamber accessible to the liquid injected by the injection head and which communicates with the outlet of the connector, the volume of said chamber varying under the effect of the displacement of the closing piston so that withdrawing the injection head causes the volume of the chamber to be reduced and excess liquid in the chamber to be expelled towards the injection outlet, wherein the closing piston is rigid and non-deformable, wherein said compression chamber is a space constituted in the housing around the closing piston and defined upstream by said end wall of the housing and downstream by a peripheral sealing gasket (referred to as the "downstream" gasket) carried by the piston, wherein the outlet of the connector is situated downstream from said gasket, and wherein the closing piston has an internal passage which presents an inlet that opens out into said space and which presents an outlet which communicates with the outlet of the connector.

The terms "upstream" and "downstream" relate here to the travel direction of the fluid going from the injection head towards the outlet of the connector.

Advantageously, the portion of the piston that moves in the inlet duct carries a peripheral sealing gasket (referred to as the "upstream" gasket) which provides sealing for the duct around the piston.

Preferably, the closing piston has a proximal portion on which both the upstream and downstream sealing gaskets are fitted, and a distal portion of tubular shape that is directed downstream.

These two portions can be made together or they can be fitted one to the other. They are advantageously molded out of synthetic resin.

Such a piston structure is remarkably simple.

In a preferred embodiment, the distal tubular portion has the internal passage of the piston passing longitudinally therethrough.

The outlet of the connector can be constituted, for example, by a catheter tube or other liquid duct permanently fixed to the connector, or else via an outlet coupling formed on the connector and which enables a catheter or other liquid duct to be coupled thereto.

Advantageously, the connector has a fixed gasket placed in the housing around the piston upstream from the outlet of the internal passage of the piston and downstream from the downstream gasket of the piston so as to define a sealed space around the piston between these two gaskets, into which space the injection liquid cannot penetrate and in which it is possible to place a spring which returns the piston upstream.

In a particular embodiment, the fixed gasket is a part disposed so as to cover the distal end of the piston with lateral sealing of the piston, said gasket having a resiliently-opening slot such that the gasket allows the piston to pass therethrough when the piston is pushed downstream by the injection head.

BRIEF DESCRIPTION OF THE DRAWINGS

Various embodiments of a coupling in accordance with the present invention are described below with reference to the figures of the accompanying drawings, in which:

FIGS. 1 to 5 are axial sections through a connector constituting a first embodiment in which the connector constitutes a base for a catheter, the section being shown for differential axial positions of the piston;

FIGS. 6 and 7 are axial sections of a connector constituting a second embodiment in which the connector does not itself constitute a base for a catheter but has an end coupling; and FIGS. 8 and 9 are axial sections of another variant of the connector.

MORE DETAILED DESCRIPTION

In the figures, elements that are identical or that correspond are designated by references that are identical or that are associated with the prime symbol.

The connectors shown in FIGS. 1 to 5 comprise a case (1) and a closing piston (5).

The case (1) defines a housing (2) that is accessible by a tubular inlet duct (3), the housing and the duct being cylindrical and on the same axis, but the right section of the housing being greater than that of the duct such that an annular shoulder (4) exists where the duct joins the chamber and constitutes an end wall at one end of the housing.

The closing piston (5) is movable in translation in the housing and in the duct, said piston carrying an upstream sealing gasket (6) in the form of an annular gasket that provides lateral sealing for the portion (5a) of the piston which moves in the inlet duct, and a downstream sealing gasket (7) in the form of an annular gasket which provides lateral sealing for the portion (5b) of the piston which moves in the housing.

The space (14) situated around the piston in the hosing and defined upstream by the end wall (4) of the housing and downstream by the sealing gasket (7) constitutes a compression chamber whose volume depends on the axial position of the piston.

The portion of the piston which defines the lateral compression chamber is advantageously designed in such a manner that the variation in the volume of this chamber (V1–V2) with displacement of the piston is maximal (FIGS. 4 and 5).

A stepped profile is easy to make and suitable for this purpose.

The inlet duct (3) is dimensioned so as to enable an injection head (8) to be inserted into the duct and, where appropriate, as far as the chamber, with lateral sealing in the duct. The duct is shaped, for example, to have a Luer type cone shape.

The closing piston has an internal passage (9) with one or more inlets (9a) opening out into the chamber (14) between the two gaskets (6) and (7) and which has one or more outlets (9b) opening out into the housing outside the piston, beyond the downstream sealing gasket.

This outlet (9b) of the internal passage of the piston is itself in communication with the outlet of the connector (13).

A fixed gasket is placed in the housing to prevent any liquid communication between the outlet of the piston (9b) and the portion of the housing situated upstream from the gasket, whatever the position of the piston. The portion of the housing between said gasket and the downstream gasket carried by the piston is thus not capable of coming into contact with the injection liquid, and a spring (12) can be placed in said portion to urge the piston upstream.

In the embodiment of FIG. 1, this gasket is constituted by the rear portion of a duck bill shaped check valve formed to engage with lateral sealing the end of the piston which includes the outlet (9b) from the passage, and which is resiliently split so as to open when said end passes and to reclose after the piston has been withdrawn, in conventional manner.

In a variant, the gasket is a simple annular gasket fixed in the housing around the piston and serving solely to provide sealing for the portion of the housing situated upstream from the outlet (9b), like the gasket (11') in the embodiment of FIGS. 10 and 11.

The case is advantageously made as two distinct portions (A) and (B) which, prior to assembly, enable the spring (12) for returning the piston upstream to be put into place in the chamber and the check valve (11) to be put into place.

The outlet from the connector can be made in various ways and the embodiments described herein are merely non-limiting examples.

In the embodiment of FIGS. 1 to 5, the outlet from the connector is constituted by the inlet (10) of a catheter tube (13) integrated in the connector, which in turn constitutes a base for the tube.

In the example of FIGS. 6 to 9, the outlet of the connector is constituted by an outlet coupling (16) which enables the base of a catheter or other duct or another coupling (16') to be releasably coupled thereto.

The portion (5a) of the closing piston (5) which closes the inlet duct (3) can be made in various ways and the embodiments described herein are merely non-limiting examples.

In the embodiments of FIGS. 1 to 7, this end (5a) of the piston is constituted by a solid cylinder which carries the upstream gasket (6) and which has sloping faces (15) at its axial end so that the opening of the inlet duct is closed in progressive manner when the piston is moved.

In the embodiment of FIGS. 8 and 9, the end (5a) of the piston is also a solid cylindrical block which carries the upstream gasket (6') but its upstream end has a slot (15') which allows liquid to pass from the injection head when the piston is reached in a position in which said slot opens out into the housing (2) of the case.

The piston can be an elongate body that is molded as a single piece, with a rear portion C forming a block which carries the two gaskets and with a front portion forming a tube D, as in the embodiments of FIGS. 1 to 7.

In a variant (FIGS. 8, 9) the tubular portion is constituted by a tube (D') that is separate and fixed to the molded body.

FIGS. 1 to 5 show the various stages in the operation of a connector of the invention:

connector at rest (FIG. 1);

beginning of the stage in which the injection head is inserted (FIG. 2);

end of the stage in which the injection head is inserted (FIG. 3); and progressive withdrawal of the injection head (FIGS. 4 and 5).

The substance injected by the injection head passes into the chamber (14) before penetrating into the internal passage of the piston. When the injection head is withdrawn, the chamber (14) is isolated from the injection head by the upstream gasket (6) as the gasket penetrates into the inlet duct (FIG. 4) so that the liquid present in the chamber is compressed and excess liquid cannot escape into the passage of the piston (FIG. 5).

The other embodiments operate in similar manner: FIG. 6 corresponds to FIG. 1, FIG. 7 corresponds to FIG. 3, and FIGS. 8 and 9 correspond to FIG. 1.

The invention is not limited to the embodiments described.

What is claimed is:

1. An automatically-closing connector for coupling an injection head to an injection outlet, in particular for medical use, the connector comprising a case which defines a housing which is accessible via an injection inlet duct opening out into the housing through an end wall of the housing, said housing communicating with an injection outlet of the connector, and the inlet duct being designed to enable the injection head to be inserted with lateral sealing into said duct towards the housing, and the connector including a rigid and non-deformable closing piston which is movable in the housing and in the inlet duct between an upstream position in which it closes the duct and towards which it is urged by resilient return means, and a downstream position in which it no longer closes the duct and towards which it is pushed by the injection head when the head is inserted into the inlet passage, the connector having a compression chamber accessible to the liquid injected by the injection head and which communicates with the outlet of the connector, the volume of said chamber varying under the effect of the displacement of the closing piston so that withdrawing the injection head causes the volume of the chamber to be reduced and excess liquid in the chamber to be expelled towards the injection outlet, wherein the closing piston is rigid and non-deformable, wherein said compression chamber is a space constituted in the housing around the closing piston and defined upstream by said end wall of the housing and downstream by a peripheral sealing gasket carried by the piston, wherein the outlet of the connector is situated downstream from said gasket, and wherein the closing piston has an internal passage which presents an inlet that opens out into the compression chamber and which presents an outlet which communicates with the injection outlet of the connector.

2. A connector according to claim 1, in which the portion of the piston that moves in the inlet duct carries a peripheral sealing gasket which provides sealing for the duct around the piston.

3. A connector according to claim 2, and in which the piston has a proximal portion on which said upstream gasket and said downstream gasket are fitted and includes a distal tubular portion directed downstream to constitute the major portion of said passage.

4. A connector according to claim 3, in which the tubular portion of the piston is constituted by a tube fitted to said proximal portion.

5. A connector according to claim 3, in which the distal portion of the piston is integrally manufactured with said proximal portion of the piston.

6. A connector according to claim 1, and which has a fixed gasket disposed in the housing around the piston upstream from said outlet of the internal passage of the piston and downstream from the downstream gasket of the piston so as to constitute a sealed space around the piston between said two gaskets, into which space the injection liquid cannot penetrate.

7. A connector according to claim 5, in which said fixed gasket is constituted by an elastically-split part designed and disposed so as to cover the piston when it is in its position for closing the inlet duct and to allow the piston to pass therethrough when the piston is pushed downstream by the injection head.

8. A connector according to claim 6, and including a spring in said sealed space for urging the piston upstream.

9. A connector according to claim 1, in which the portion of the piston which defines the compression chamber is shaped in such a manner that the variation in the volume of the compression chamber is maximal.

10. A connector according to claim 1, in which said portion of the piston has a stepped profile.

11. A connector according to claim 1, in which the outlet is constituted by the inlet of a catheter tube integrated in the connector.

12. A connector according to claim 1, in which the outlet is constituted by an outlet coupling.

13. A connector according to claim 1, in which said end wall of the housing defines an annular shoulder around the outlet of said duct in the housing, which shoulder defines the upstream end of the compression chamber.

14. A connector according to claim 1, in which the outlet is constituted by the inlet of a duct in a liquid pathway for enabling liquid to be introduced into the body.

* * * * *